United States Patent
St. Pierre et al.

(10) Patent No.: US 7,063,717 B2
(45) Date of Patent: Jun. 20, 2006

(54) BIOINTERFERENCE SCREW FIXATION TECHNIQUE

(75) Inventors: Patrick St. Pierre, Alexandria, VA (US); Jeffrey Wyman, Naples, FL (US); Reinhold Schmieding, Naples, FL (US); Philip S. O'Quinn, Naples, FL (US)

(73) Assignee: Arthrex, Inc., Naples, FL (US)

( * ) Notice: Subject to any disclaimer, the term of this patent is extended or adjusted under 35 U.S.C. 154(b) by 588 days.

(21) Appl. No.: 10/256,076

(22) Filed: Sep. 27, 2002

(65) Prior Publication Data

US 2003/0028194 A1 Feb. 6, 2003

Related U.S. Application Data

(63) Continuation-in-part of application No. 09/864,258, filed on May 25, 2001, now Pat. No. 6,461,373.

(60) Provisional application No. 60/207,235, filed on May 26, 2000.

(51) Int. Cl.
*A61B 17/04* (2006.01)

(52) U.S. Cl. .......... 606/232; 606/72; 606/104

(58) Field of Classification Search .......... 606/72, 606/73, 23, 104; 623/13.11–13.14
See application file for complete search history.

(56) References Cited

U.S. PATENT DOCUMENTS

| | | | |
|---|---|---|---|
| 4,927,421 A | * | 5/1990 | Goble et al. .......... 606/73 |
| 5,603,716 A | | 2/1997 | Morgan et al. |
| 5,632,748 A | | 5/1997 | Beck, Jr. et al. |
| 5,643,320 A | | 7/1997 | Lower et al. |
| 5,662,658 A | | 9/1997 | Wentstrom, Jr. |
| 5,720,766 A | | 2/1998 | Zange et al. |
| 5,733,307 A | | 3/1998 | Dinsdale |
| 5,871,504 A | | 2/1999 | Eaton et al. |
| 6,273,890 B1 | | 8/2001 | Frazier |
| 6,319,270 B1 | | 11/2001 | Grafton et al. |
| 6,355,053 B1 | | 3/2002 | Li |
| 6,355,066 B1 | | 3/2002 | Kim |
| 6,461,373 B1 | * | 10/2002 | Wyman et al. .......... 606/232 |
| 6,527,794 B1 | * | 3/2003 | McDevitt et al. .......... 606/232 |
| 6,733,529 B1 | * | 5/2004 | Whelan .......... 606/72 |

* cited by examiner

*Primary Examiner*—Julian W. Woo
(74) *Attorney, Agent, or Firm*—Dickstein Shapiro Morin & Oshinsky LLP

(57) ABSTRACT

Endosteal fixation of a ligament graft with an interference fixation device installed in a retrograde manner in ACL reconstruction is disclosed. The interference fixation device may be a screw or a ribbed implant fitted with a length of reinforced suture or wire for pulling the interference fixation device through the tibial tunnel. The suture extends beyond the leading tip of the interference fixation device a sufficient length to allow the interference fixation device to be passed into the joint by pulling on the suture or wire exiting the tibial tunnel. A driver or an impaction device, such as a slap hammer, is employed to advance and insert the interference fixation device in a retrograde manner into the tibial tunnel. Accordingly, interference fixation of the graft near the tibial plateau is provided, thereby eliminating graft abrasion at the tibial plateau tunnel opening.

1 Claim, 3 Drawing Sheets

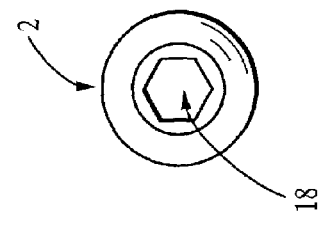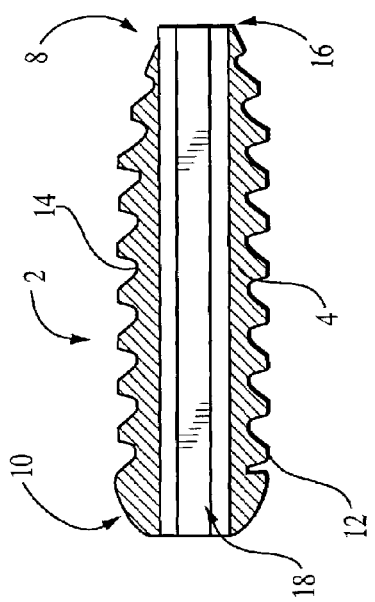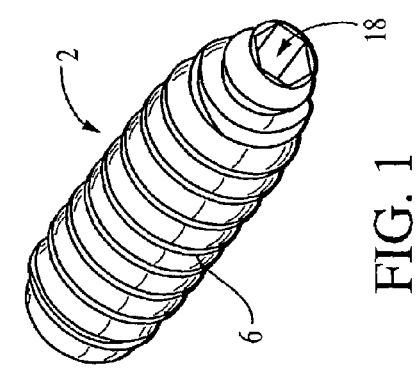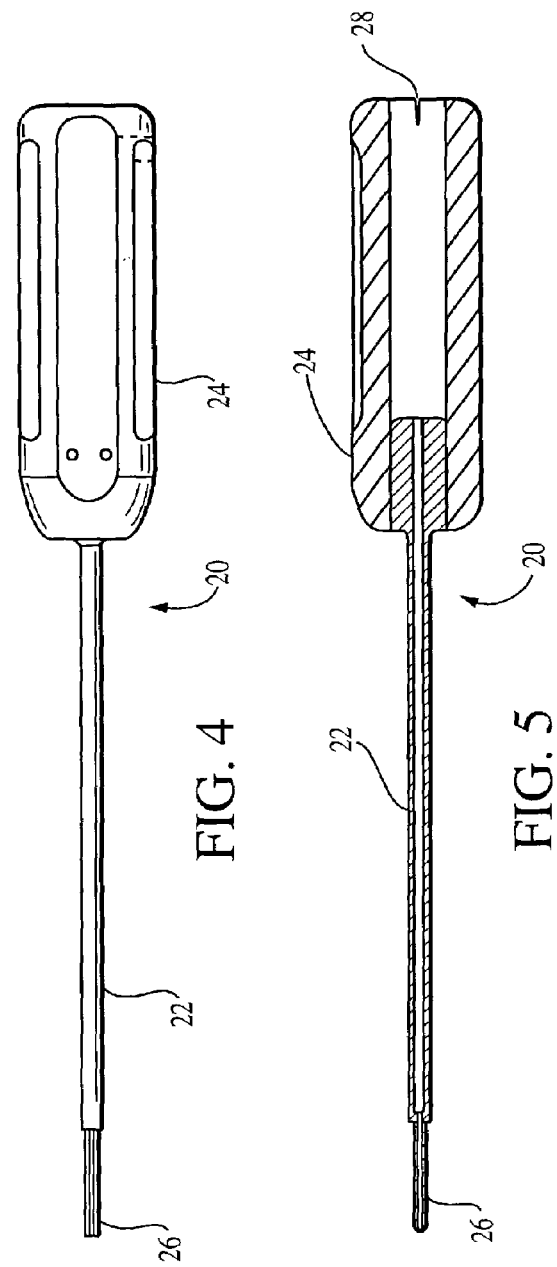

BIOINTERFERENCE SCREW FIXATION TECHNIQUE

This application is a continuation-in-part of U.S. application Ser. No. 09/864,258, filed May 25, 2001, now U.S. Pat. No. 6,461,373, and claims the benefit of U.S. Provisional Application Ser. No. 60/207,235, filed May 26, 2000.

FIELD OF THE INVENTION

The present invention relates to interference screw fixation of replacement ligament grafts, and more particularly to methods and apparatus for retrograde placement and installation of an interference screw for graft fixation in a bone tunnel.

BACKGROUND OF THE INVENTION

Methods of anterior cruciate ligament (ACL) reconstruction using interference screw fixation are described in U.S. Pat. Nos. 5,211,647 and 5,320,626, the entire disclosures of which are incorporated herein by reference. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like. Accurate positioning of the tibial and femoral tunnels requires a drill guide, such as those disclosed in U.S. Pat. Nos. 5,269,786 and 5,350,383, which also are incorporated herein by reference.

One drawback of the described tenodesis methods is that the ligament graft is secured only at the bottom of the tibial tunnel. The graft is not secured at the top end of the tibial tunnel. Consequently, the graft is free to move from side to side, resulting in a "windshield wiper" effect, during which the graft abrades against the upper rim of the tibial tunnel, shortening the life of the ACL repair.

U.S. Pat. No. 5,603,716 to Morgan et al. discloses a technique for ACL reconstruction that avoids the above-noted problem of graft abrasion. The method disclosed by Morgan et al. requires forming two closed-ended sockets, one in the tibia and the other in the femur.

Accordingly, the need exists for a method of ACL reconstruction that provides anatomical graft fixation at the tibial plateau, and without the need for forming two separate bone sockets.

SUMMARY OF THE INVENTION

The present invention overcomes the disadvantages of the prior art, such as those noted above, by providing methods and apparatus for endosteal fixation of a ligament graft using an interference fixation device that is installed in a retrograde manner. In a preferred embodiment, anterior cruciate ligament (ACL) reconstruction is performed using an interference screw installed in a retrograde manner through the tibial plateau to secure an ACL graft at the top of the tibial tunnel.

The interference fixation screw is fitted with a length of suture to provide a means for pulling the screw into the tibial tunnel through the tibial plateau. The suture preferably passes through the length of the screw and engages the trailing end of the screw. The suture is secured to the screw using at least one of a knot, an adhesive, insert molding, and equivalent securing methods. The suture extends beyond the leading tip of the screw a sufficient length to allow the suture to be passed through the tibial tunnel and to be grasped for pulling the screw into the top opening of the tunnel. The screw and suture preferably are bioabsorbable.

A driver for the screw fits into a drive opening in the leading end of the screw. Preferably, the driver is cannulated to accept the length of suture extending from the bottom opening of the tibial tunnel, and has means for grasping the suture to assist the surgeon in pulling the interference screw into the top opening of the tibial tunnel.

According to a preferred method of the present invention, after the ligament graft has been placed in the tibial tunnel, the suture extending from the interference screw is fed into the joint cavity, into the top, tibial plateau opening of the tunnel, and down through the tibial tunnel to exit at the anterior surface of the tibia. The free end of suture exiting the anterior surface of the tibial tunnel preferably is captured within the cannulated driver. Alternatively, a knot could be formed on the end of the suture to secure the suture to the driver, or a separate suture puller could be used within the scope of the present invention.

Drawing on the suture using the driver at the anterior opening of the tibial tunnel pulls the interference screw into the joint cavity in a retrograde fashion. The knee joint is positioned to allow the end of the screw to be manipulated into the top opening of the tibial tunnel, with the screw being pivoted within the joint cavity to align axially with the tunnel and the driver.

With the screw being drawn into a position of alignment with the tunnel, the driver is advanced into the tibial tunnel. Pulling on the suture retains the screw in position for engagement with the driver by applying tension to the suture in the direction opposing driver insertion.

Once the driver has engaged the screw, turning the driver causes the screw to advance, or "back in" to the tunnel in retrograde fashion. Using a right-threaded screw, a surgeon will turn the screw counter-clockwise. In an alternative embodiment, the screw has reverse threads, so that turning the driver clockwise advances the screw into the tunnel. The screw is turned into the tunnel until the back end of the screw is substantially flush with the tibial plateau, and has been installed to a depth sufficient to provide interference fixation of the graft at the top of the tunnel. The driver is disengaged from the screw, and excess suture is removed.

According to another embodiment of the present invention, anterior cruciate ligament (ACL) reconstruction is conducting using an interference implant which is inserted in a retrograde manner through the tibial plateau by employing an impaction device such as a slap hammer, to secure an ACL graft at the top of the tibial tunnel. In this embodiment, the implant is preferably inserted using a strand, such as a reinforced suture or a wire. Once the ligament graft has been placed in the tibial tunnel, the suture or wire extending from the interference implant is fed into the joint cavity, into the top tibial plateau opening of the tunnel, and down through the tibial tunnel to exit at the anterior surface of the tibia. However, the free end of suture or wire exiting the anterior surface of the tibial tunnel is not captured with a driver, as in the previously described embodiment, but rather with an engaging device, for example a hook or a clam, that further engages the free end of the suture or wire to an impaction device, preferably a surgical slap hammer.

Drawing on the suture or wire at the anterior opening of the tibial tunnel pulls the interference implant into the joint cavity in a retrograde fashion and allows the implant to be manipulated into the top opening of the tibial tunnel, with the implant being pivoted within the joint cavity to align axially with the tunnel. With the implant drawn in a position of alignment with the tunnel, the slap hammer is repeatedly tapped for sufficient time and with sufficient force to advance the implant into the tibial tunnel in a retrograde fashion. Once the implant is inserted within the tibial tunnel so that the back end of the implant is substantially flush with the tibial plateau and the implant provides interference fixation of the graft at the top of the tibial tunnel, the impaction and engaging devices are disengaged and the suture or wire is removed.

Other features and advantages of the present invention will become apparent from the following description of the invention which refers to the accompanying drawings.

BRIEF DESCRIPTION OF THE DRAWINGS

FIG. 1 is a perspective view of a bio-tenodesis screw according to the present invention.

FIG. 2 is a cross-sectional elevation of the screw of FIG. 1.

FIG. 3 is a proximal end view of the screw of FIGS. 1 and 2.

FIG. 4 is an elevation of a driver for the screw of FIGS. 1–3 according to the present invention.

FIG. 5 is a cross-sectional plan view of the driver of FIG. 4.

DETAILED DESCRIPTION OF THE PREFERRED EMBODIMENTS

Figure 6:
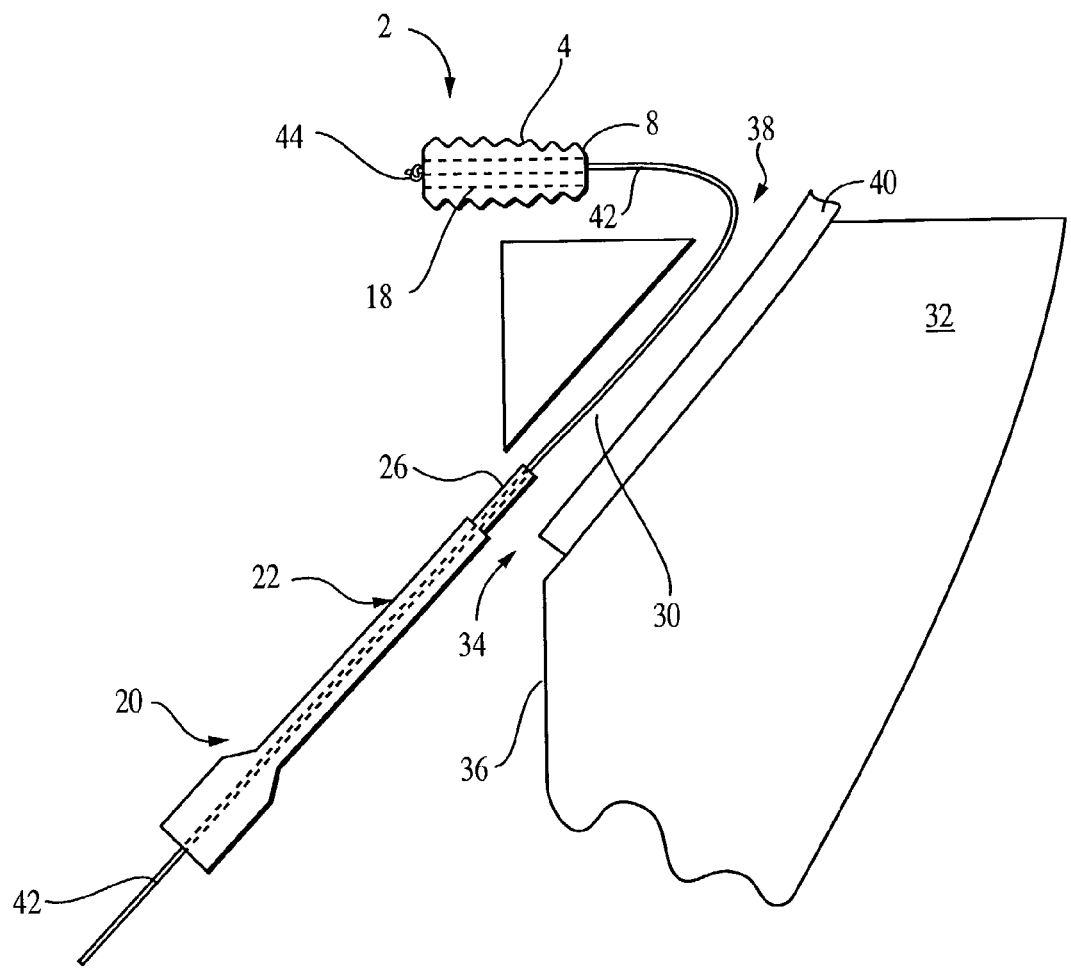
FIG. 6 schematically illustrates fixation of an ACL graft using the retrograde biointerference screw of the present invention, and in accordance with one embodiment of the invention.

Referring initially to FIGS. 1–3, a bioabsorbable interference screw 2 for tenodesis of an anterior cruciate ligament graft is shown. Body 4 of the screw 2 features a continuous thread 6 provided substantially along the length of the body from a blunt front end 8 to a rounded back end 10. The thread preferably has flattened crests 12 and flattened troughs 14 to obviate ligament graft damage by the screw threads and enhance graft fixation.

The cannulated body 4 tapers toward the front end 8 to terminate in a blunt tip 16. The taper eases entry of the screw into the tibial tunnel according to the preferred method of ligament graft fixation described further below. The blunt tip 16 of the screw prevents damage of the ligment graft during insertion of the screw. The rounded back end 10 of the screw minimizes abrasion and wear of the installed ligament graft. Cannula 18 formed through screw body 4 has a hexagonal shape for engaging a driver described below. Preferably, cannula 18 is straight, although a tapered cannula could be used. The hexagonal shape of cannula 18 is shown clearly in FIG. 3. The preferred screw is 23 mm long, and is supplied in various diameters.

Referring to FIGS. 4 and 5, a driver 20 for installing the interference screw is shown. Driver 20 includes a cannulated shaft 22 secured permanently to a cannulated handle 24. A drive tip 26 formed at the distal end of shaft 22 has a straight, hexagonal shape conforming to cannula 18 of screw 2. At the proximal end of the handle, notches 28 are provided on either side for securing suture.

A method of ACL tenodesis according to a preferred embodiment of the present invention includes forming a tunnel 30 in a tibia 32, as shown in FIG. 6. The tunnel is formed with a diameter appropriate for interference fixation based on the size of the selected screw 2. Tunnel 30 ascends at an angle posteriorly from a bottom opening 34 at an anterior tibial surface 36 toward an upper opening 38 at the tibial plateau. The lower end of an ACL graft 40 is inserted into the tunnel through the tibial plateau.

The length of suture 42 passing through interference screw 2 is secured at the back end of the screw using a knot 44, for example. Screw 2 is inserted into the joint and through the tunnel 30 so that a free end of the suture exits the bottom opening 34. Suture passing instruments as are known can be utilized.

The free end of the suture is used to draw screw 2 toward the tibial opening 38, either by hand or using driver 20 by threading the suture into the driver 20 and securing the suture in notches 28, for example. With the knee joint distended, the screw 2 is manipulated into the tibial plateau opening 38 and pivoted into axial alignment with the tunnel 30. Driver 20 is advanced into the tunnel 30 to achieve engagement with screw 2. Turning the screw with the driver advances the screw into the tunnel 30 in a retrograde manner. Screw insertion is continued until the back end 10 of screw 2 is substantially flush with the tibial plateau and the graft 40 is secured sufficiently within the tunnel. The driver 20 and any excess suture 4 is removed from the tunnel to complete this portion of the procedure.

Figure 7:
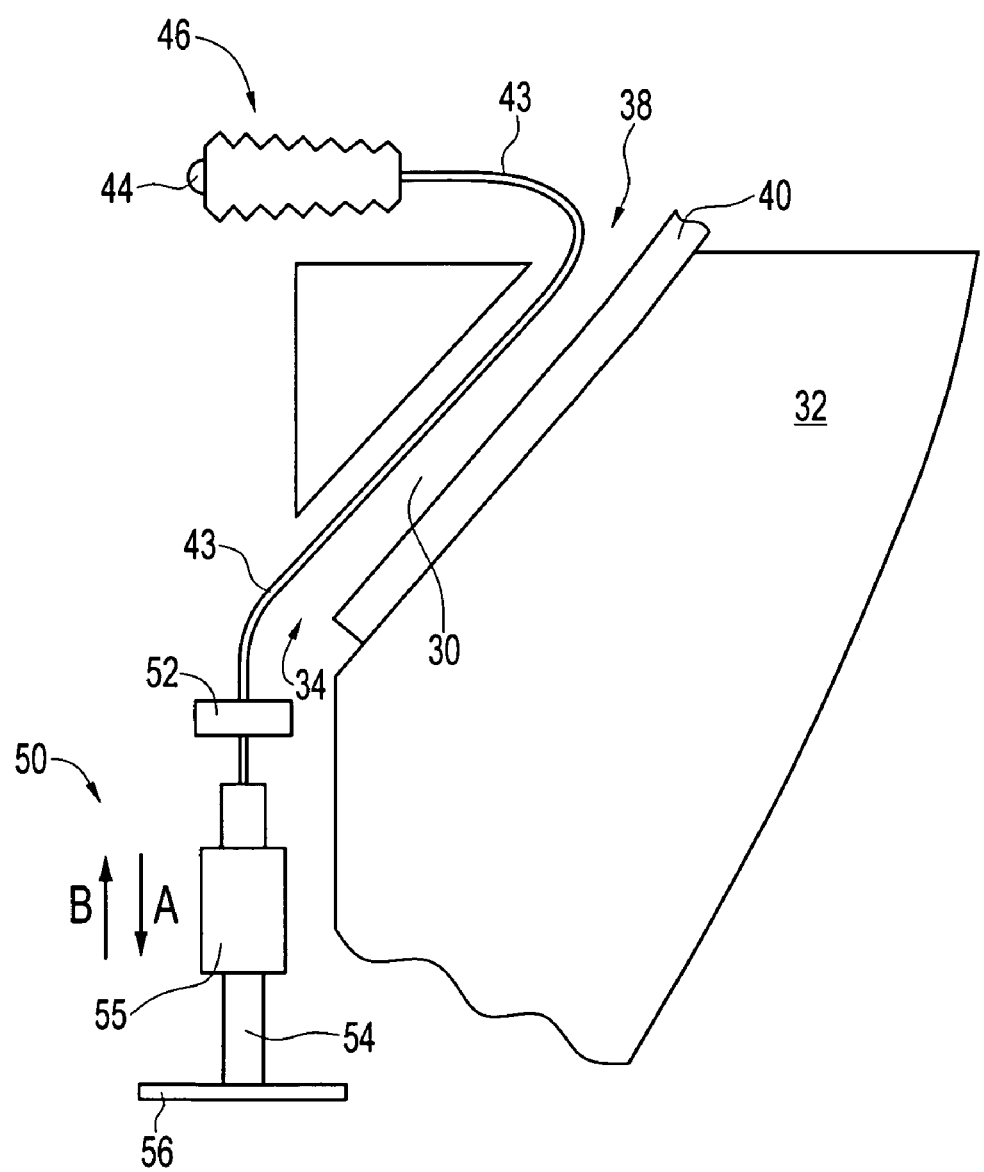
FIG. 7 schematically illustrates fixation of an ACL graft using a retrograde interference implant of the present invention, and in accordance with another embodiment of the invention.

In yet another embodiment of the present invention and as illustrated in FIG. 7, a ribbed or barbed bioabsorbable interference implant 46 for anterior cruciate ligament (ACL) reconstruction may be inserted and impacted in a retrograde manner through the tibial tunnel 30 by employing an impaction device 50. According to one embodiment of the present invention, the impaction device 50 may be a surgical slap hammer having an elongated and cylindrical configuration. As illustrated in FIG. 7, the slap hammer 50 is provided with a body member 55 which is slidably positioned over barrel member 54. At one end, the barrel member 54 is provided with an enlarged collar or stop 56 having a diameter greater that the diameter of the body member 55. At the other end, the barrel member 54 is connected to an engaging device 52, for example a hook or a clamp. The engaging device 52 allows one end of strand 43, for example, a reinforced suture or wire, to be secured to the slap hammer 50. The other end of the reinforced suture or wire 43 is secured to the bioabsorbable interference implant 46 by a ball 44 (FIG. 7) or any other fixation device of various shapes and geometries.

Once the ligament graft 40 has been placed in the tibial tunnel 30, the suture or wire extending from the interference implant 46 is fed into the joint cavity, into the tibial plateau opening of the tunnel 30, and down through the tibial tunnel 30 to exit at the bottom opening 34, as in the previously first described embodiment. If reinforced suture is employed, a suture passing instrument may be employed to feed the reinforced suture as described above. The free end of suture or wire 43 is captured with the engaging device 52 to further engage and connect the free end of the suture or wire 43 to the surgical slap hammer 50.

Drawing on the suture or wire 43 at the anterior opening of the tibial tunnel 30 is conducted by gently and repeatedly tapping the slap hammer 50 to pull the interference implant 46 into the joint cavity in a retrograde fashion and to allow the implant 46 to be manipulated into the upper opening 38 of the tibial tunnel 30. The slap hammer 50 is gently tapped to allow the body member 55 to travel back-and-forth in a vertical or oblique direction designated by arrows A, B (FIG. 7) and to repeatedly stop on the collar 56 and pull the suture or wire 43. In this manner, the interference implant 46 is pivoted within the joint cavity for axial alignment with the tunnel 30.

With the interference implant 46 axially aligned with the tibial tunnel 30, the slap hammer 50 is tapped for sufficient time and with sufficient force to allow the implant 46 to advance into the tibial tunnel 30 in a retrograde fashion against graft 40. One skilled in the art will realize that the amount of force for tapping the slap hammer 50 is directly proportional to the diameter and length of the interference implant 46, as well as the length of the tibial tunnel 30. Impaction of the interference implant 46 is continued until the back end of the implant 46 is substantially flush with the tibial plateau and the implant 46 provides sufficient fixation of the graft 40 within the tibial tunnel 30. The slap hammer 50 and the engaging device 52 are subsequently disengaged and the suture or wire is removed.

Although the above described embodiment has been illustrated with reference to a slap hammer having an elongated and cylindrical form, the present invention is not limited to this embodiment and contemplates other impaction devices and/or surgical hammers of various geometries and configurations, as desired.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of anterior cruciate ligament reconstruction, the method comprising the steps of:
    forming a tibial tunnel between an anterior tibial surface and the tibial plateau;
    placing a ligament graft in the tibial tunnel;
    feeding a length of strand extending from and attached to an interference implant into the joint cavity and down through the tibial tunnel by way of the opening in the tibial plateau;
    drawing on the free end of strand exiting the anterior surface of the tibial tunnel to pull the interference implant into the joint cavity in a retrograde fashion;
    engaging the free end of strand to an impaction device;
    allowing the end of the interference implant to be manipulated into the top opening of the tibial tunnel, with the interference implant being pivoted within the joint cavity to align axially with the tunnel; and
    inserting the interference implant into the tunnel.

* * * * *